United States Patent
Sadeghi et al.

(10) Patent No.: US 6,687,685 B1
(45) Date of Patent: Feb. 3, 2004

(54) AUTOMATED MEDICAL DECISION MAKING UTILIZING BAYESIAN NETWORK KNOWLEDGE DOMAIN MODELING

(75) Inventors: Sarmad Sadeghi, Houston, TX (US); Afsaneh Barzi, Houston, TX (US); Neda Zarrin-Khameh, Houston, TX (US)

(73) Assignee: Dr. Red Duke, Inc., Houston, TX (US)

(*) Notice: Subject to any disclaimer, the term of this patent is extended or adjusted under 35 U.S.C. 154(b) by 0 days.

(21) Appl. No.: 09/544,953

(22) Filed: Apr. 7, 2000

(51) Int. Cl.[7] ............................................. G06F 15/18
(52) U.S. Cl. ........................ 706/15; 706/45; 706/924; 600/300
(58) Field of Search ............................ 706/15, 45, 52, 706/59, 924, 61, 20, 60, 48, 50; 600/300

(56) References Cited

U.S. PATENT DOCUMENTS

| | | | | |
|---|---|---|---|---|
| 4,839,822 A | * | 6/1989 | Dormond et al. | 706/45 |
| 4,872,122 A | * | 10/1989 | Altschuler et al. | 356/432 |
| 5,005,143 A | * | 4/1991 | Altschuler et al. | 702/181 |
| 5,133,046 A | | 7/1992 | Kaplan | 706/52 |
| 5,307,263 A | | 4/1994 | Brown | 600/301 |
| 5,331,550 A | * | 7/1994 | Stafford et al. | 382/128 |
| 5,471,382 A | * | 11/1995 | Tallman et al. | 600/300 |
| 5,594,638 A | | 1/1997 | Iliff | 705/3 |
| 5,660,176 A | * | 8/1997 | Iliff | 600/300 |
| 5,680,866 A | * | 10/1997 | Kangas et al. | 600/483 |
| 5,715,374 A | * | 2/1998 | Heckerman et al. | 706/46 |
| 5,764,923 A | | 6/1998 | Tallman et al. | 705/3 |
| 5,800,347 A | | 9/1998 | Skates et al. | 600/300 |
| 5,802,256 A | | 9/1998 | Heckerman et al. | 706/59 |
| 5,827,180 A | | 10/1998 | Goodman | 600/300 |
| 5,922,079 A | | 7/1999 | Booth et al. | 714/26 |
| 5,930,803 A | | 7/1999 | Beker et al. | 707/104.1 |
| 5,950,632 A | | 9/1999 | Reber et al. | 128/898 |
| 5,951,469 A | | 9/1999 | Yamaura | 600/300 |
| 5,964,700 A | | 10/1999 | Tallman et al. | 600/300 |
| 6,014,626 A | * | 1/2000 | Cohen | 704/275 |
| 6,067,466 A | * | 5/2000 | Selker et al. | 600/513 |
| 6,076,083 A | * | 6/2000 | Baker | 706/52 |
| 6,081,786 A | * | 6/2000 | Barry et al. | 705/3 |
| 6,083,173 A | * | 7/2000 | Grant et al. | 600/529 |
| 6,090,044 A | * | 7/2000 | Bishop et al. | 600/300 |
| 6,154,736 A | * | 11/2000 | Chickering et al. | 706/59 |
| 6,188,988 B1 | * | 2/2001 | Barry et al. | 705/3 |
| 6,456,622 B1 | * | 9/2002 | Skaanning et al. | 370/389 |
| 6,556,977 B1 | * | 4/2003 | Lapointe et al. | 706/15 |
| 6,601,055 B1 | * | 7/2003 | Roberts | 706/45 |
| 2001/0023419 A1 | * | 9/2001 | Lapointe et al. | 706/15 |
| 2002/0044296 A1 | * | 4/2002 | Skaanning | 358/1.14 |
| 2002/0052559 A1 | * | 5/2002 | Watrous | 600/528 |
| 2002/0107824 A1 | * | 8/2002 | Ahmed | 706/46 |
| 2003/0105731 A1 | * | 6/2003 | Lapointe et al. | 706/15 |
| 2003/0130973 A1 | * | 7/2003 | Sumner et al. | 706/45 |

OTHER PUBLICATIONS

Tax et al., "Learning Structure with Many–Take–All Networks", Artificial Neural Networks, pp. 95–101, 1996.*

(List continued on next page.)

*Primary Examiner*—Wilbert L. Starks, Jr.
*Assistant Examiner*—Kelvin Booker
(74) *Attorney, Agent, or Firm*—Andrew G. DiNovo

(57) ABSTRACT

The present invention relates to a system and method of medical knowledge domain modeling and automated medical decision-making, such as for online, questionnaire-based medical triage. In the present invention, information such as conditions and characteristics related to a diagnosis or disposition level is modeled in a Bayesian Network. The Bayesian Network may comprise instantiable nodes, fault nodes, intermediary nodes, a utility node and a decision node. Using Bayesian inference, the conditional probability of any pair in the network may be determined in real-time. These conditional probabilities are modified upon the input of evidence, which is typically in the form of answers to a dynamic set of questions designed to identify a diagnosis or disposition level for the patient under evaluation.

23 Claims, 9 Drawing Sheets

OTHER PUBLICATIONS

Wiegerinck et al., "PROMEDAS, A Prototype Decision Support System for Medical Diagnosis", Foundation for Neural Networks SNN, 1998, Retrieved from the Internet: http://www.snn.kun.nl/nijmegen/diagnosis-graph.p.*

Wiegerinck et al., "A Bridge between Mean Field Theory and Exact Inference in Probilistic Graphical Models", Foundation fo Neural Networks: SNN, 2000, Retrieved from the Internet: http://www.snn.kun.nl/nijmegen/diagnosis-graph.p.*

Wiegerinck et al., "Inference and Advisory System for Medical Diagnosis Second Report STW–NGN55.3614", Foundation for Neural Networks: SNN, Apr. 1999, Retrieved from the Internet: http://www.snn.kun.nl/nijmegen/diagnosis-graph.p.*

Wiegerinck et al., "PROMEDAS: Probabilistic Medical Diagnostic Advisory System", Google Internet Search, Jan. 1996, Retrieved from the Internet on Nov. 5, 2002, Retrieved from: Http://www.mbfys.kun.nl/snn/nijmegen/diagnosis-graph.*

Burg et al., "A Diagnostic Advice System based on Pathophysiological Models of Diseases", NEC Research Index, Medical Informatics Europe, 1999.*

Haddawy et al., "Clinical Simulation Using Context–Sensitive Temporal Probability Models", NEC Research Index, Proceedings of the 19th Annual Symposium on Computer Applications in Medical Care, 1995.*

Ogunyemi et al., "Probabilistically Predicting Penetrating Injury for Decision Support", IEEE Xplore, Proceedings of the 11th IEEE Symposium on Computer–Based Medical Systems, Jun. 1998, pp. 44–49.*

Ngo et al., "A Knowledge–Based Model Construction Approach to Medical Decision Making", NEC Research Index, Proceeding of the 1996 AMIA Annual Fall Symposium, 1996.*

Wiegerinck et al., "Apporximate Inference for Medical Diagnosis", NEC Research Index, Pattern Recognition Letters, No. 20, 1999, pp. 1231–1239.*

Lam et al., "Learning Bayesian Belief Networks: An Approach Based on The MDL Principle", NEC Research Index, Computational Intelligence, Vol 10, Jul. 1994, pp. 269–293.*

Kozlov et al., "A Parallel Lauritzen–Spiegelhalter Algorithm for Probabilistic Inference", IEEE Xplorer, Proceedings of Supercomputing, Nov. 1994, pp. 320–329.*

Beuscart et al., "Bayesian Networks for Antibiotics Prescription", Proceedings of the 1st Joint BMES/EMBS Conference Servin Humanity, Advancing Technology, vol. 2, Oct. 1999, p. 856.*

Folckers et al., "An Intelligent Problem Solving Environment for Designing Explanation Models and for Diagnostic Reasoning in Probabilistic Domains", Intelligent Tutoring Systems, 1996, pp. 353–362.*

Macus, H.J., "Deriving a Bayesian Probability Network from Data", NEC Research Index, MIT Department of Computer Scienc May 1991, pp. 1–70.*

* cited by examiner

| Finding1 ▼ | Labelled ▼ | Sex | | |
|---|---|---|---|---|
| Chief Sample | DDx1 | DDx2 | DDx3 | DDx4 |
| male | 0.333333 | 0.5 | 0.5 | 0.666667 |
| female | 0.666667 | 0.5 | 0.5 | 0.333333 |

| Complaint | ▼ | Labelled | ▼ | Abdominal Pain |
|---|---|---|---|---|
| Medical Risk | \multicolumn{2}{c}{false} | \multicolumn{2}{c}{true} | |
| Surgical Risk | false | true | false | true |
| DDx1 | 8 | 0 | 8 | 0 |
| DDx2 | 1 | 1 | 1 | 1 |
| DDx3 | 0 | 8 | 0 | 8 |
| DDx4 | 1 | 1 | 1 | 1 |

| Complaint | ▼ | Labelled | ▼ | Abdominal Pain |
|---|---|---|---|---|
| Risk Factor | Surgical Risk | Medical Risk | No Risk | |
| DDx1 | 8 | 8 | 8 | |
| DDx2 | 1 | 1 | 1 | |
| DDx3 | 0 | 0 | 0 | |
| DDx4 | 1 | 1 | 1 | |

AUTOMATED MEDICAL DECISION MAKING UTILIZING BAYESIAN NETWORK KNOWLEDGE DOMAIN MODELING

I. FIELD OF THE INVENTION

This invention relates generally to the field of medicine, and more particularly to methods of self-diagnosis and evaluation, particularly in connection with automated medical decision-making, including online triage.

II. RELATED ART

Spiraling medical care costs in this country have become a well-known problem, and particularly with respect to emergency care. Studies show that approximately half of emergency room patients are not in need of urgent care.[1] Expense of treatment could be significantly reduced if those patients were assisted in determining whether they are suffering from an emergent condition prior to going to the emergency room.

[1] U.S. Department of Health and Human Services, "National Hospital Ambulatory Medical Care Survey: 1992 Emergency Department Summary," DHHS Publication No. (PHS) 96-1786 (March 1997).

On the other hand, a significant number of patients unduly delay their visit to the emergency room after the onset of symptoms, wasting critical hours. For example, it is estimated that over 40% of heart attack patients wait more than four hours before seeking medical help, increasing the risk of damage to the heart. In addition, the cost and complications relating to providing medical care to such patients soars.

Additionally, many patients who are suffering from an emergent condition and who go to emergency rooms are there because they have not properly managed their chronic conditions, such as diabetes, asthma, hypertension, or heart disease. In addition, expense in treating such patients goes well beyond the emergency room. It is believed that such patients are the largest overall contributors to overall medical expense, much of which could be reduced if the disease were better monitored and controlled.

There has therefore arisen a need in the medical industry for a means for enabling people who are not medically trained to ascertain their condition and evaluate whether it requires emergency care, or what other level of care is appropriate. There has further arisen a need for new system for disease management, and more particularly to a method of facilitating self-monitoring and management of chronic health conditions.

Various prior art methodologies have been developed for achieving the foregoing objectives. One such prior art technique is known as telephone triage.[2] With telephone triage, a patient calls a number which is answered by a health care professional, who may be a doctor or a nurse. The health care professional then walks the patient through a series or pre-formulated questions, and then makes a medical judgment as to whether the patient should seek emergency care.

[2] See, e.g., Wheeler, Sheila Quilter, "Telephone Triage Protocols," (1998).

Conventional telephone triage, while reasonably effective, has certain disadvantages. First, a trained health care professional is required to answer the phone, adding to the cost of the system. When the system is too busy, the patient will experience delays in what may be a critical time. When the system is not busy, the time of the health care professional manning the line is wasted, resulting in increased expense. In addition, human judgment is necessarily interposed in the process, which may result in dissimilar and potentially inaccurate advice being given to patients. In addition, the system is imperfectly dynamic, and oftentimes questions are asked which are not the most significant or meaningful.

An improvement of traditional telephone triage is described in U.S. Pat. No. 5,764,923 to Tallman et al. The Tallman patent discloses what is known in the art as "computer-assisted medical decision making." It discloses a medical network management system wherein patients access a team of health care professionals over the telephone. The health care professionals assess patient conditions with the assistance of an automated set of assessment algorithms. While the invention disclosed in Tallman may provide certain efficiencies, the system still requires the presence of a team of health care professionals, and ultimately relies on the individual medical judgment of the person answering the phone. In addition, Tallman discloses no specific systematic methodology for developing the algorithms upon which it relies.

Another prior art system for self-evaluation and disease management is described in U.S. Pat. No. 5,827,180 to Goodman. The Goodman patent describes a health network wherein information pertaining to a patient is shared between a health care provider, a treatment facility and a patient. The information may pertain to treatment instructions specific to each patient. The system requires a treatment plan specific to each patient.

While the system described in Goodman may assist in disease management, it suffers from some drawbacks. The system in Goodman must be established for treatment of a patient on a patient-specific basis. Algorithms are developed specific to treatment of that patient, not to the disease. A person who has not established a presence on the Goodman system could not obtain any assistance in terms of self-diagnosis, treatment or disease management. Moreover, Goodman contemplates communication to the patient with a pager, which is less convenient and more intrusive than online systems.

Online medical services are also in the prior art. For example, Dr. Schueler's Health Informatics, Inc., operates a website. At that website, a user can gain medical information, and from such information, the user may attempt to determine the nature of his or her condition. That website does not, however, offer online triage or utilize the disposition level of the present invention.

Attempts to model medical knowledge in automated format have typically taken the form of so-called "rule-based" systems. Rule-based systems are normally configured as a series (often very complex) of if x, then y type rules. While formidable rule-based systems have been constructed, they have their shortcomings. One of the primary shortcomings is the tremendous pace at which such systems grow when an additional layer of variables is added. Another is their difficulty in addressing uncertainty.

There has therefore arisen a need for a reliable, statistically sound and convenient method for automated triage and disease management, particularly in an online environment, without the direct involvement of health care professionals. There has further arisen a need for a consistent, systematic methodology for evaluating the statistic significance of responses in connection with such an automated triage system for assisting users in determining the nature of their condition and facilitating disease management.

III. BRIEF DESCRIPTION OF THE DRAWINGS

The present invention is illustrated by way of example, and not by way of limitation, in the figures of the accompanying drawings and in which like reference numerals refer to like elements and in which.

IV. DESCRIPTION OF A PREFERRED EMBODIMENT

The present invention relates to automated medical triage. For the purposes of discussion, this description will focus on automated triage over a network of computers such as the Internet. A person skilled in the art, however, would recognize that the methods and systems discussed herein will apply equally to other automated systems, such as phone networks, or to software programs residing on a user's computer or designed for use on a single computer, such as with a CD-ROM disc.

Generally, the automated triage system to which the present invention relates operates as follows. A user is concerned about symptoms being experienced, and is considering seeking emergency or other medical care. Through a personal computer and the Internet, the user accesses a server which contains software routines designed to accomplish medical triage. Alternatively, the user can access the system via telephone or other conventional medium. The user is presented with a series of questions and prompted to give an answer. The series of questions is dynamic and interactive, insofar as responses to previous questions cause the later questions to change and focus on particular conditions. Once the answers obtained from the questions are statistically sufficient, a decision is determined, the user may be provided with information about his or her condition, and a recommendation may be made with respect to obtaining further medical attention.

In another embodiment of the present invention, the interactive questionnaire is supplemented with information received from medical devices attached to the computer of the user. Such medical devices may include a blood pressure monitor, heart rate monitor, temperature monitor, respiratory rate monitor, blood glucose monitor, peak flow monitor, electrocardiogram device, monitor for detecting concentration of gases such as oxygen, carbon dioxide and carbon monoxide in the expired air, or any number of other devices intended to supply information about the patient's medical condition. The information is conveyed through the Internet to the server, where it is used in connection with the questionnaire to supplement the decision. In a preferred embodiment, the system uses the information obtained from the medical devices 1, 2 and user database 50 to formulate the series of questions to the user and further enhance the interactive nature of the Internet triage.

The questionnaire presented to the user is a series of questions specifically developed to address particular user concerns. For example, one question set may pertain to the general condition of chest pain. As the patient answers questions, certain conditions are statistically eliminated, and other questions are presented to continue the diagnostic process. The questionnaire thus reflects a dynamic response to changes in the knowledge set, and is used for determining, for example, the condition of the patient and what kind of medical care or other services are needed.

Figure 1:
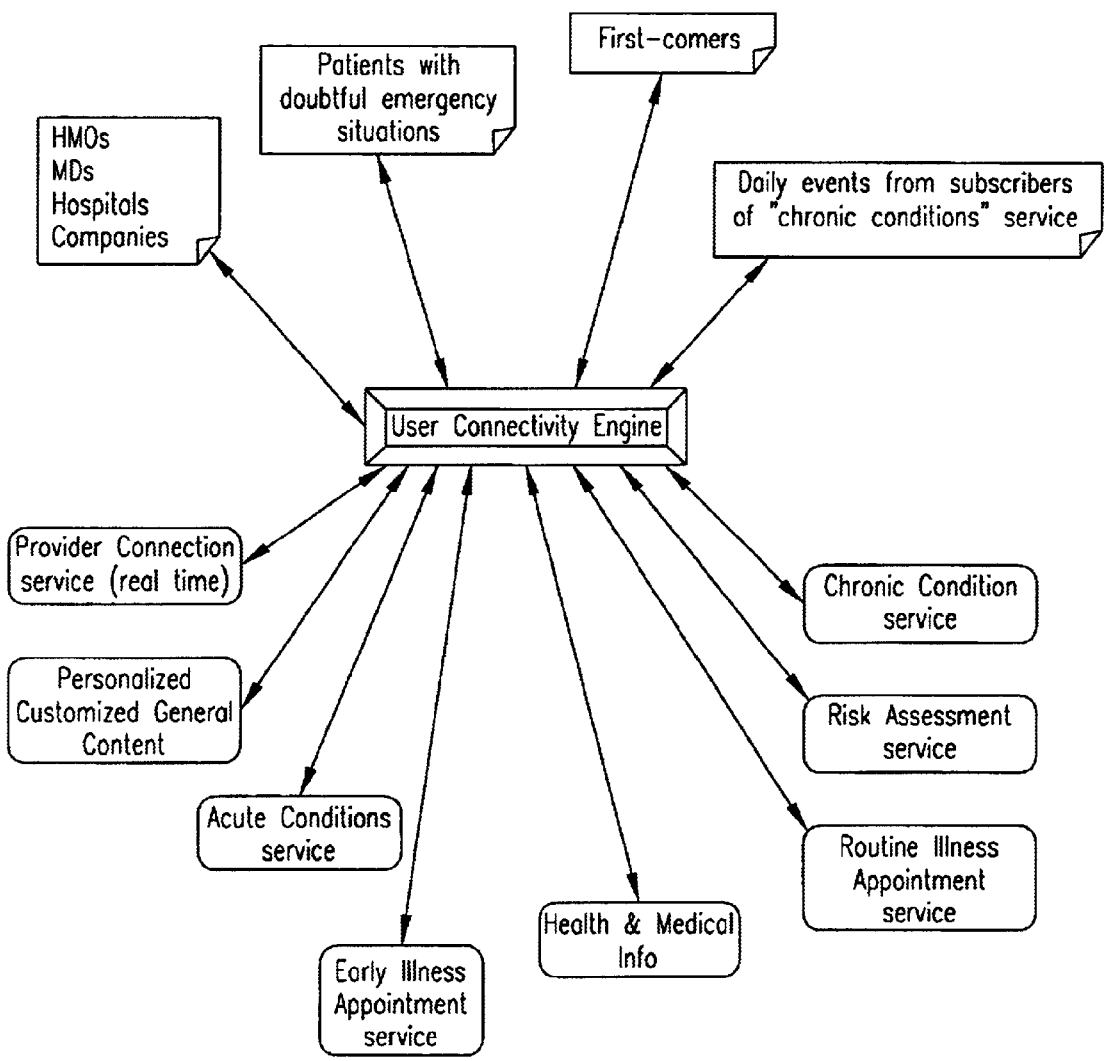
FIG. 1 is a flow chart showing information flow in an online embodiment of the present invention.

Turning to the figures, FIG. 1 shows the spectrum of users of the triage system of the present invention implemented in the on-line environment. As can be seen by reference to FIG. 1, users of the system might include patients with doubtful emergency situations, HMO's, doctors, hospitals, drug companies, first-comers, and chronic patients. A variety of services may be provided by the system, including personalized content, acute conditions service, chronic condition service, and other services related to medical care.

Figure 2:
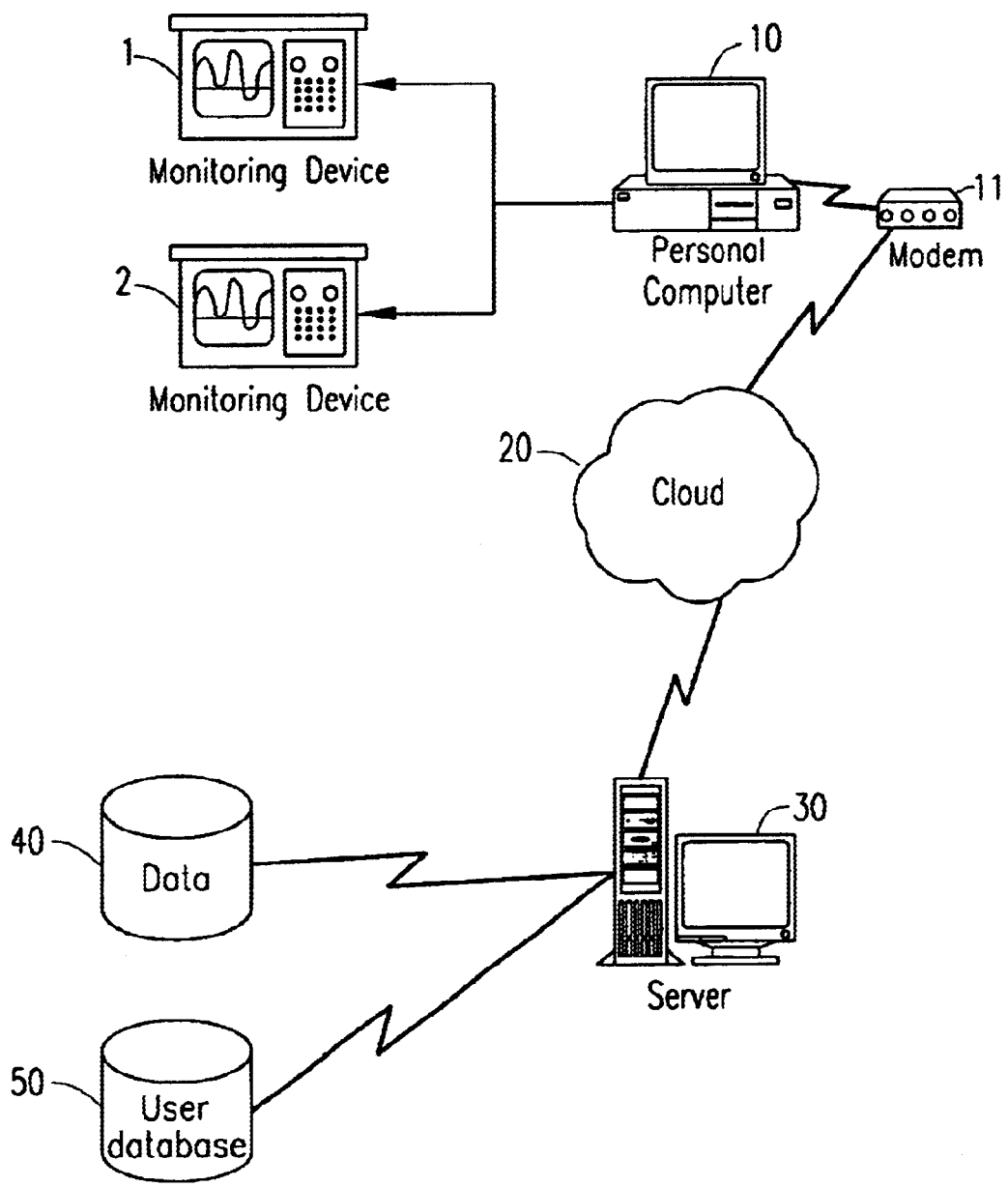
FIG. 2 is a diagram of an exemplary base system of online triage using the present invention.

Referring to FIG. 2, a basic system of the present invention is illustrated. A user (not shown) may access a personal computer 10 for purposes of obtaining online triage. While a desktop computer is shown, it will be apparent to those skilled in the art that a laptop computer, handheld computer, or similar device with a display or other user interface may also be used. The personal computer 10 accesses server 30 through cloud 20, where cloud represents a varying path through a network of computers such as the Internet. In an alternative embodiment, personal computer 10 accesses server 30 through a dedicated line or communication path, or through a network.

Server 30 runs the Bayesian Network of the present invention, and is in communication with a series of databases 40 containing the algorithms and questionnaires for various medical conditions. Server 30 extracts appropriate algorithms and questions from database 40 in response to answers and/or medical data supplied by the user and medical devices 1, 2 which may be attached to or in communication with the user and attached to computer 10 through serial or other ports (not shown). Server 30 runs the algorithm suited to the user's need and provides the user with information as to the user's medical condition, treatment, and whether emergency care should be sought.

This invention relates to a methodology for building medical decision-making tools for a number of major chief complaints is explained. In the context of the present invention, "medical decision making" refers to any of several medical-related decisions, including patient diagnosis, disposition level, prognosis, surgical, medical or ambulatory treatment, or the like. As used herein, the "chief complaint" is the presenting complaint of a patient using the system or making an outpatient visit. An example of a chief complaint is abdominal pain.

Network Structure

In Bayesian Networks, instead of modeling "rules" for decision-making, the domain "knowledge" is modeled. In this way, the information is presented in the form of probabilities, and efficient algorithms that are part of Bayesian Networks will propagate the evidence entered into any point in the network to the rest of the network.

Bayesian Inference $$P(A/B) = \frac{P(B/A) \cdot P(A)}{P(B)}$$

By using Bayesian inference rules that are derived from the original Bayes Theorem, the network any conditional probability provided in the network using the following, well-established relationship.

By switching evidence A and B in the above equation, the converse conditional probability may also be expressed.

Nodes

The building blocks of the Bayesian Network are "nodes." Nodes are linked to one another using directed edges. The only limitation on the number and form of these directed edges is that in the resulting graph, there should not be a complete cycle. The domain knowledge for the nodes is provided in the form of a probability table that is modified in real time based upon the evidence introduced to the network.

Nodes in the Bayesian Network of the present invention may be generally categorized into 5 types:

1. Instantiable Nodes: These nodes are nodes into which evidence is entered. Usually, they will correspond to questions with discrete or continuous input that are instantiated by the user; i.e., evidence "observed" by the user will be entered to the network at these nodes.

2. Fault Nodes: These are output nodes, the results of which are of interest to the user. Decisions and the information sought to be provided by the network are modeled in these nodes. These nodes are not instantiated. They are monitored for answers that are needed. In a network, there can be more than one fault node, and as a result, fault nodes may be interpreted in conjunction or separately. For example, in a medical network, one fault node could provide the diagnosis or disposition level, and another fault node could provide the overall prognosis for the patient.

3. Intermediary Nodes: These nodes are neither instantiated nor monitored or faulted. Their purpose is grouping and at times simplifying they overall network design.

4. Utility Nodes: These nodes will be in close interaction with nodes and provides the quantitative background for decision node to make a decision. The utility node comprises a table of values representing utilities for various decisions given a state in the chief complaint fault node. A decision node calculates a utility value for all states in the decision node. To do this, the decision node uses the table of corresponding utility values for all states in the chief complaint fault node.

5. Decision Nodes: These nodes are fault nodes, therefore, the methodology described here is not considered a single fault node model, as it in fact uses at least two fault nodes and if more decisions are associated with the algorithm, then more than two nodes will be fault nodes. The decision node will have different decisions as its states. At any given time based on probabilities for different states in the diagnosis fault node and table of utilities in the utility node a utility value will be calculated for all states of the decision node. Utilities are provided such that the state with greatest utility will be considered the best decision. Decisions could be of any nature. Examples include a triage situation where the goal would be to find out if the user of systems needs to call for an ambulance, drive to emergency room, see a doctor or stay at home. Alternatively, in an outpatient or office visit, the decision could be of the type "Does this patient need to be hospitalized or not?" or "What is the best set of paraclinical evaluation including imaging and lab tests for a particular patient?"

There is no inconsistency for interpretation of a Bayesian Network of this type; in some instances, however, interpretation of multiple faults can be problematic. An example would be a network that provides chances of a patient having appendicitis and perforated peptic ulcer in 2 separate fault nodes. A sample run of this network could provide a 90% chance of appendicitis, and a 90% chance of perforated peptic ulcer, which is difficult to interpret.

In the preferred embodiment of the present invention discussed below, it is taught how to model medical knowledge in the form of a Bayesian Network in a way that is reasonably clear-cut, efficient, easily maintainable, promptly expandable, robust, and computationally viable. It should be emphasized that the Bayesian Network of the present invention is not limited to single fault modeling. Instead of merely monitoring a fault node, the utility node and decision node work in conjunction to actually generate a decision of interest.

Diagnosis Node

A fault node, this node will provide the post-test probabilities for possible causes for the presenting symptom. At time index zero, i.e., when only the chief complaint or the main presenting symptom is known—e.g., headache or chest pain—this special node will reflect the prevalence of different causative factors in the sub-population of people having the symptom.

In addition to or in lieu of a diagnosis node, a decision node can be used. A decision node might identify a diagnosis or a disposition level, which corresponds to the urgency of medical attention required by the patient. Four disposition levels might be used: ambulance, emergency room, doctor visit, and home care. Of course, other decision nodes could be identified. For example, the decision node could also provide insight as to the prognosis of the patient in a clinical situation if so designed. In this way, based upon the information in the domain and evidence instantiated for a patient, the network could decide the prognosis or outcome of the patent. This is particularly useful in CCU, it is important to know if the patient is in a critical situation, or is in danger of deadly arrhythmias, or in ICU circumstances, when we would like to know if the patient is at increased risk of infection, etc.

Figure 3:
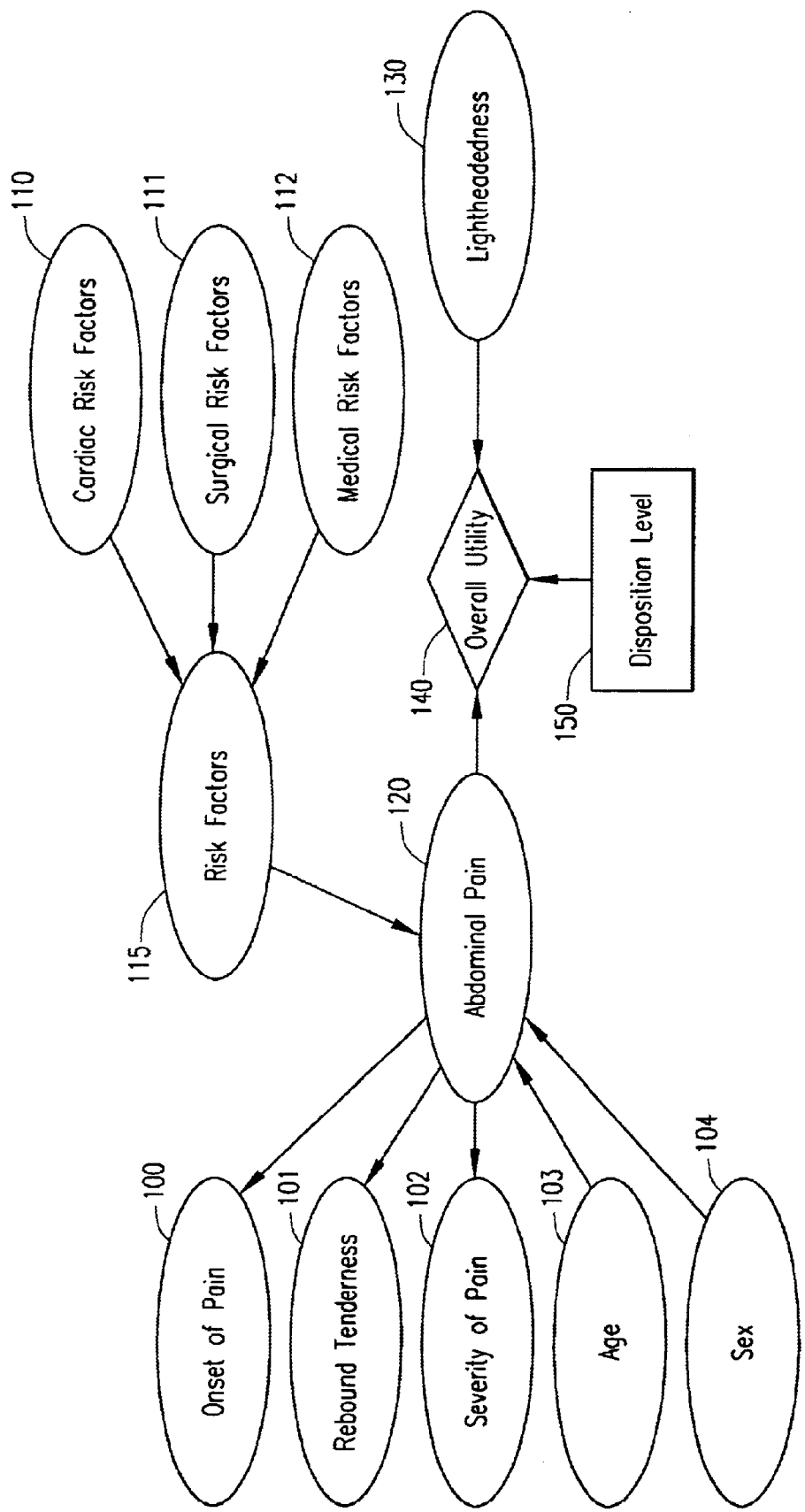
FIG. 3 is a Bayesian Network showing instantiable nodes, fault nodes, an intermediary node, a decision node and a utility node.

Referring to FIG. 3, we can see the primary types of nodes used in the network. Instantiable nodes 100, 101, 102, 103 and 104 express evidence to abdominal fault node 120. Intermediary nodes for cardiac risk factors 110, surgical risk factors 111, and medical risk factors 112 express evidence to intermediary risk factor node 115, which in turn expresses evidence on abdominal fault node 120.

As can be seen, abdominal fault node 120 expresses evidence on utility node 140, as does a special variety of instantiable node, lightheadedness instantiable node 130. Unlike the other instantiable nodes shown in FIG. 3, lightheadedness instantiable node 130 can change the decision (i.e., the disposition), without changing abdominal pain fault node 120. Finally, disposition decision node 150 is implicitly joined with utility node 140.

Information in the Medical Domain

In the medical domain, there are many different pieces of information that could be used to arrive at a diagnosis. These include: symptoms, signs, CBC, X-rays, blood pressure, history of smoking, family history, ethnic background, etc. For purposes of a domain description and classification of input information, all various pieces of information could be classified into 2 groups with relatively little conceptual overlap:

A. Presentations Potentially Caused by the Disease Process

These are events that can be observed in the context of certain disease processes with a higher probability than in the normal population. This could range from a slightly elevated frequency of the finding in the afflicted population than in the normal population to presentations that are highly specific to a certain disease process and are virtually non-existent in the normal population. Also, this category includes presentations observable by patients, by experts, or through sophisticated para-clinical techniques. Therefore the following classes of medical findings fall in this broad category:

1. Symptoms, observable by both doctor and patient, such as coughing.
2. Signs, observable by doctors, such as retinal hemorrhage.
3. Lab tests, observable by a specialist using laboratory test kits, such as elevated hematocrit.
4. Imaging findings, observable by a radiologist, such as hilar calcification of pulmonary lymph nodes.
5. Pathology findings, observable by a pathologist, such as malignant cells.

All of the above-mentioned findings are implemented similarly in a knowledge representation of the domain. When modeling the information in the domain about this category, one would normally have to provide answers to questions in the form "What is the frequency of finding $F_i$ in the context of disease $DDx_j$?" As shown in Table-1, the table of information for this category containing information about frequency or the conditional probability of findings in the context of diseases. See Table-1.

TABLE 1

This table provides information on frequencies of findings in the context of diseases, where F: Finding, P: Probability, DDx: Differential Diagnosis

|  | $DDx_1$ | $DDx_2$ | ... | $DDx_n$ |
|---|---|---|---|---|
| $F_1$ | $P(F_1 \mid DDx_1)$ | $P(F_1 \mid DDx_2)$ | ... | $P(F_1 \mid DDx_n)$ |
| $F_2$ | $P(F_2 \mid DDx_1)$ | $P(F_2 \mid DDx_2)$ | ... | $P(F_2 \mid DDx_n)$ |
| ... | ... | ... | ... | ... |
| $F_m$ | $P(F_m \mid DDx_1)$ | $P(F_m \mid DDx_2)$ | ... | $P(F_m \mid DDx_n)$ |

Figure 4:
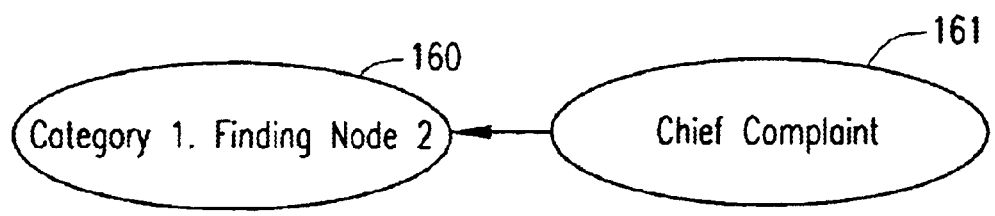
FIG. 4 is a Bayesian Network no de diagram representation of a category 1 finding.

FIG. 4 depicts the Bayesian Network representation of a category 1 finding, wherein instantiable node 160 implicitly asserts evidence on chief complaint fault node 161.

TABLE 2

Table of frequencies for Finding Node in FIG. 1.

| Chief Complaint | DDx1 | DDx2 | DDx3 | DDx4 |
|---|---|---|---|---|
| F1 Finding 1 | 0.25 | 0.25 | 0.25 | 0.25 |
| F1 Finding 2 | 0.25 | 0.25 | 0.25 | 0.25 |
| F1 Finding 3 | 0.25 | 0.25 | 0.25 | 0.25 |
| F1 Finding 4 | 0.25 | 0.25 | 0.25 | 0.25 |

Table-2, above, is the table of frequencies for the Finding Node in FIG. 4. For all differential diagnoses, $DDx_i$ probabilities for all different states of the Finding Node are provided.

B. Presentations and Factors Changing the Distribution of Diseases

Sometimes, events in the domain have such strong effects on the domain that they change the frequencies of diseases drastically. Sex, for example, could drastically change the distribution of causes for abdominal pain by ruling out all gynecological problems in males, thereby significantly changing the distribution of diseases accounting for abdominal pain. The following classes of medical findings fit in this category:

1. Risk factors, observable by doctors and patients, like sex, age group, etc.
2. Diagnostic symptoms, signs, or other clinical/lab/imaging findings that clearly identify certain diagnosis for the clinical problem.
3. Syndromes, a group of medical findings that are highly suggestive of certain diagnosis for the clinical problem.

When modeling the information in the domain about this category, the network must be provided the answer to the following question: "What is the frequencies of diseases $DDx_l$ to $DDx_n$ if finding $F_i$ is present?"

A table of information for this category will contain information about the frequencies of diseases in the context of certain background events. See Table-3, below.

TABLE 3

Provides information on frequencies of diseases in the context of background events and risk factors, where F: Finding, P: Probability, DDx: Differential Diagnosis

|  | $F_1$ | $F_2$ | ... | $F_m$ |
|---|---|---|---|---|
| $DDx_1$ | $P(DDx_1 \mid F_1)$ | $P(DDx_1 \mid F_2)$ | ... | $P(DDx_1 \mid F_m)$ |
| $DDx_2$ | $P(DDx_2 \mid F_1)$ | $P(DDx_2 \mid F_2)$ | ... | $P(DDx_2 \mid F_m)$ |
| ... | ... | ... | ... | ... |
| $DDx_n$ | $P(DDx_n \mid F_1)$ | $P(DDx_n \mid F_2)$ | ... | $P(DDx_n \mid F_m)$ |

Figure 5:
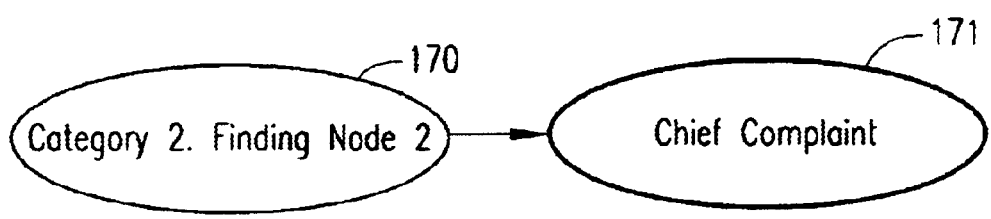
FIG. 5 is a Bayesian Network node diagram representation of a category 2 finding.

FIG. 5 shows the Bayesian Network representation of a category 2 finding, in which instantiable node 170 explicitly exerts evidence on chief complaint fault node 171.

TABLE 4

Table of frequencies for Finding Node in FIG. 1. For all findings in Finding Node we have to provide information on the probabilities of all differential diagnoses, $DDx_i$.

| Category Fl | F1 Finding 1 | F1 Finding 2 | F1 Finding 3 | F1 Finding 4 |
|---|---|---|---|---|
| DDx1 | 0.25 | 0.25 | 0.25 | 0.25 |
| DDx2 | 0.25 | 0.25 | 0.25 | 0.25 |
| DDx3 | 0.25 | 0.25 | 0.25 | 0.25 |
| DDx4 | 0.25 | 0.25 | 0.25 | 0.25 |

Implicit vs. Explicit Effects of Findings on Probabilities of Diseases

Referring now to Table-1 and Table-3, it is apparent to one of ordinary skill in the art that, bearing Bayes Theorem in mind, each of the two tables may be converted into the other. However, choices are made on the basis of available information. For instance, from published medical literature it is known that prevalence of diseases differs based on sex, age, and the presence or absence of certain other risk factors. Therefore, meaningful distributions may be provided.

Generally, evidence from instantiable nodes may be exerted on fault nodes explicitly or implicitly. When exerted explicitly, the parent node (the node from which the arrow is directed) expresses its evidence in terms of probabilities in the table associated with the child node. In such an explicit relationship, the table in the child node grows exponentially, since it must contemplate every explicit expression it might receive from a plurality of parent nodes. In an implicit relationship, on the other hand, the probability changes resulting from the child node are not explicitly reflected on the parent node. In this instance, the Bayesian Network must calculate the changes in probabilities, and is actively working and calculating as needed for decision nodes and the like.

For signs and symptoms, information can be provided about frequencies in a given disease (e.g., the frequency of vomiting as a symptom in a patient with appendicitis). This sort of relationship is referred to as a "category 1" relationship. The reverse can also be done in a "category 2" relationship, i.e., providing frequencies of certain diseases in the context of a symptom (e.g., the frequency with which a person who is vomiting has appendicitis). For a series of reasons, however, a prevalence of category 2 relationships is not the preferred embodiment.

1. If one were to provide information about possible differential diagnoses in the context of a sign, symptom or any medical finding in the first category, the result is a very long list of differential diagnoses, a good portion of which do not fit in the model under construction. For instance, it is known that in the abdominal pain model, a certain percentage of people presenting with abdominal pain could have vomiting. However, DDx for vomiting are beyond DDx for abdominal pain, and include many brain diseases and metabolic disorders.
2. In addition to the non-specific nature of such symptoms and their chances of being present in numerous medical situations, there are a mandatory minimum number of differential diagnoses that must be accounted for in the context of any symptom so the sum of frequencies will be 1. But, if the reverse is done, one can include as many differential diagnoses as desired, and the prior probabilities for this list will be provided in the context of the corresponding chief complaint.
3. It is simpler to provide information on the frequencies of different levels or attributes of a symptom in the context of a disease, rather than providing probabilities for different diseases in the context of a certain level or attribute of a presenting symptom. For example, it is simpler to provide probabilities on frequencies of mild, moderate, and severe pain in the context of appendicitis rather than providing probabilities of various differential diagnoses such as appendicitis for mild, moderate, and severe pain.
4. If one were to model m binary symptoms for a chief complaint in the explicit format, one would be required to provide information on the probabilities of n differential diagnoses for chief complaint x, and to provide numbers for all possible combinations of absence or presence of the n symptoms. This would result in a table of frequencies with the size $n \cdot 2^m$. Clearly, as m grows, the table becomes exponentially larger. Whereas, if the model is implemented implicitly, one would have to provide $2 \cdot m \cdot n$ numbers only, which grows linearly with respect to m.

Figure 6:
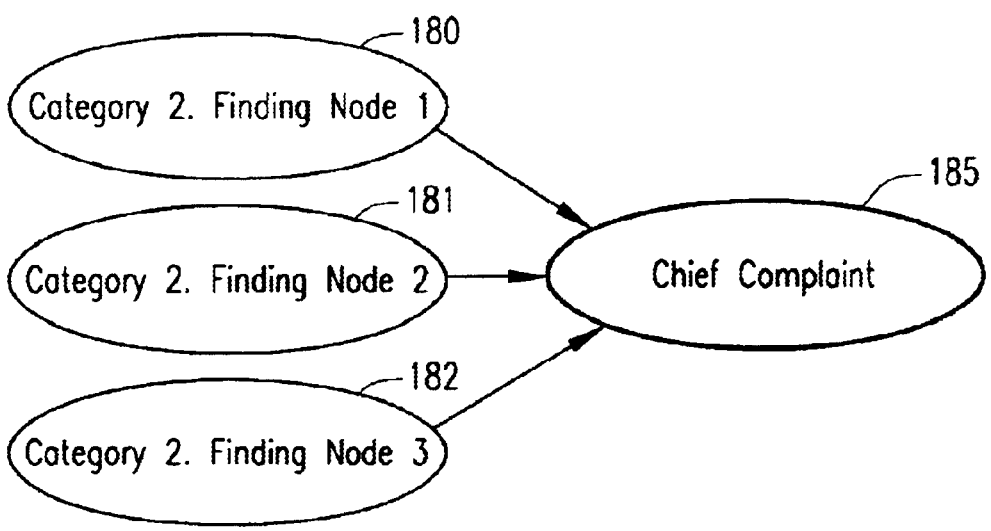
FIG. 6 is a Bayesian Network no de diagram showing an implementation model used to explicitly exert the effects of findings on a fault node.

FIG. 6 shows an implementation model which is useful to explicitly exert the effects of findings from instantiable nodes 180, 181 and 182 on a node, which in this example is the chief complaint fault node 185. The implementation is shown below in Table-5. The table is formed in the chief complaint fault node 185. Although in this model one can explicitly address effects of a finding on the distribution of states of another node, there is one drawback to it. The table size grows exponentially and therefore, factors to implement in this way should be judiciously picked or else the network will be very difficult to design and maintain.

TABLE 5

The table formed in the chief complaint node.

| Caegory 2 F1 | false | | | | true | | | |
|---|---|---|---|---|---|---|---|---|
| Caegory 2 F1 | false | | true | | false | | true | |
| Caegory 2 F1 | false | true | false | true | false | true | false | true |
| DDx1 | 0.25 | 0.25 | 0.25 | 0.25 | 0.25 | 0.25 | 0.25 | 0.25 |
| DDx2 | 0.25 | 0.25 | 0.25 | 0.25 | 0.25 | 0.25 | 0.25 | 0.25 |
| DDx3 | 0.25 | 0.25 | 0.25 | 0.25 | 0.25 | 0.25 | 0.25 | 0.25 |
| DDx4 | 0.25 | 0.25 | 0.25 | 0.25 | 0.25 | 0.25 | 0.25 | 0.25 |

Figure 7:
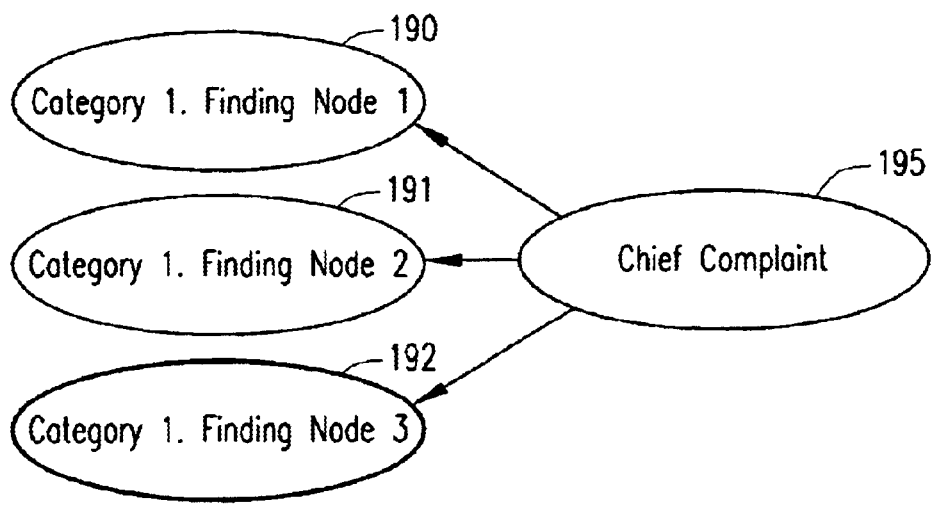
FIG. 7 is a Bayesian Network node diagram used to implicitly exert the effects of findings on a fault node.

Referring now to FIG. 7, the implementation model represented therein is useful when effects of findings (such as those input into instantiable nodes 190, 191 and 192) can be implicitly exerted on a node. In the example shown, the node is chief complaint fault node 195. The table for implementing FIG. 7 is shown below in Table-6. The table is formed in the finding nodes. The limitation of this model is that the probabilities for states of the fault node in the presence of different combinations of states of three instantiable nodes 190, 191 and 192 cannot be expressed explicitly. They will be calculated in the run time, and therefore may not reflect the dramatic effects of certain combination of findings on the probabilities of chief complaint fault node 195.

TABLE 6

The table formed in the finding nodes implementing FIG. 7.

| Chief Complaint | DDx1 | DDx2 | DDx3 | DDx4 |
|---|---|---|---|---|
| false | 0.25 | 0.25 | 0.25 | 0.25 |
| true | 0.25 | 0.25 | 0.25 | 0.25 |

Overlap Between the Two Categories and Rules of Thumb to Make a Decision as to Which Should be Used for a Particular Finding As shown, some findings in medicine can be implemented in both ways. In such instances, making a decision regarding how to implement the finding in the domain can become difficult and not only the performance, but also the maintainability and expandability of the network may depend on it.

Below are set forth some useful rules of thumb, it being understood by one of ordinary skill in the art that one may diverge from these generalized rules when appropriate.

Rules of Thumb

1. Which one of the two questions is more meaningful? If either one, implement it accordingly. If both are roughly equal, continue to rule 2.

2. Could the states in the node coexist? If not, then the node can be instantiated and one of the states will be present while the others are absent. To determine how to implement such nodes, consider rule 3. If states in the node can coexist, then the node is not instantiable, and should be modeled as an intermediary node. For each of the states in such a node, there should be a corresponding node connected to this node. To determine how to implement such intermediary nodes and the corresponding group of instantiable nodes, consider rule 4. Also see the discussion under the heading Intermediary Nodes and Domain Simplification.

3. If a change in states in the instantiable node does not dramatically change probabilities in the other node (in this case, a fault node), then they are best implemented implicitly. An example making a certain state in the fault node four times more probable that other states given a certain state in the instantiable node, which is considered a dramatic change. If we know a certain state in the fault node is more probable given a state in the instantiable node, however, then this is not a dramatic change. Such cases, as explained, are best implemented implicitly.

4. Intermediary nodes and their "satellite" nodes should be arranged such that intermediary nodes will not receive inward edges from satellites nodes and other nodes (in this case, a fault node). If this happens, unless the intermediary node is instantiated, the evidence will not propagate to the fault node because of the d-separation of the satellite node and fault node. Having observed this rule, the same concepts set forth in rule 3 can be applied to determine explicit or implicit implementation of the nodes. First, determine how the intermediary node should be implemented. If it should be explicit, then determine how each of the satellite nodes should be implemented. If it should be implemented implicitly, however, then it is mandatory that all satellite nodes be implemented implicitly. This is to prevent d-separation. It should be noted that d-separation between satellite nodes of the intermediary node is not of any particular concern, since evidence is still propagated to the fault node. It should also be pointed out that this methodology could be applied to multiple levels of intermediary nodes, too, be they explicit or implicit.

As explained above, it is typically preferable to implement the domain implicitly, rather than explicitly. An example would further clarify this issue. While modeling domain A, it becomes necessary to include an observable node instantiating the subject's sex. The information available in the domain tells us that sex has no effects on $DDx_2$ and $DDx_3$, however, $DDx_1$ is twice as common in females as in males, and $DDx_4$ is twice as common in males as in females.

Figure 8:
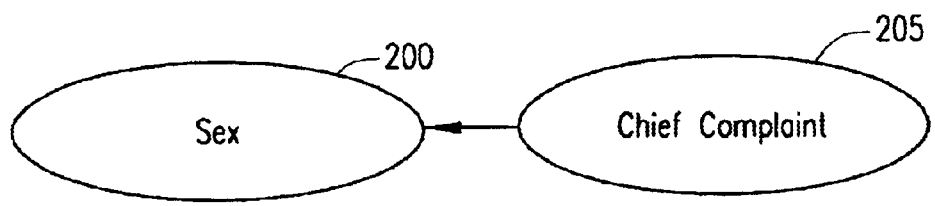
FIG. 8 is a Bayesian Network node diagram showing the implicit modeling effects of sex on the fault node named "chief complaint."

To implement this effect, the model shown in FIG. 8 is built. From FIG. 8, one can better understand the implicit modeling effects of sex on the chief complaint fault node 205. FIG. 8 represents the table generated in the instantiable node 200 related to sex.

Figure 9:
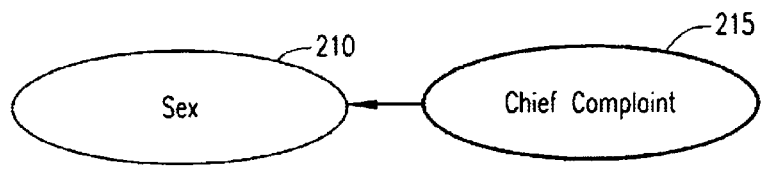
FIG. 9 is a Bayesian Network node diagram showing the explicit modeling effects of sex on the fault node named "chief complaint."

In contrast, assume that in modeling domain B, the information available is in the form: "It is known that: (i) $DDx_3$ is absent in males; and (ii) the most common cause of the chief complaint in males is $DDx_1$, with an 80% chance; and (iii) $DDx_2$ and $DDx_4$ each have an equal chance of 10%. For females: (i) $DDx_1$ is absent; (ii) the most common cause of the chief complaint is $DDx_3$, with an 80% chance; and (iii) $DDx_2$ and $DDx_4$ each have an equal chance of 10%." For this domain, the model shown in FIG. 9 may be implemented. FIG. 9 shows the explicit modeling effects of instantiable node 210 (for sex) on the chief complaint fault node 215.

Special Combinations of Findings: Syndromes

Sometimes, despite the fact that findings have implicitly or explicitly expressed effects for or against certain diagnoses, and are not by themselves diagnostic for any state in the fault node, among hundreds of combinations that are possible for the findings, few of those combinations are highly suggestive of a certain state in the fault node. In medicine, such findings are called syndromes. To implement syndromes in a Bayesian Network and still maintain the independent effects of findings on the fault node, and yet detect the syndrome combination, the following model may be used. In this model, finding $F_4$ in Findings Node 1 and 2 are suggestive of $DDx_4$ and $DDx_1$ respectively as isolated events. But as joint events, they are diagnostic of $DDx_3$, the probability of which is less than 1% if the two findings were isolated.

Figure 10:
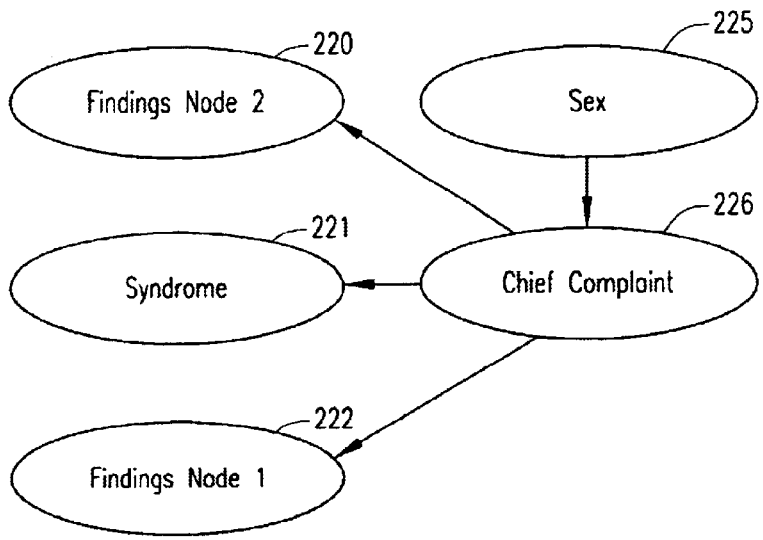
FIG. 10 is a Bayesian Network node diagram and correlated probability table showing the effects of inputting F4 in Findings Node 1 as evidence.
Figure 11:
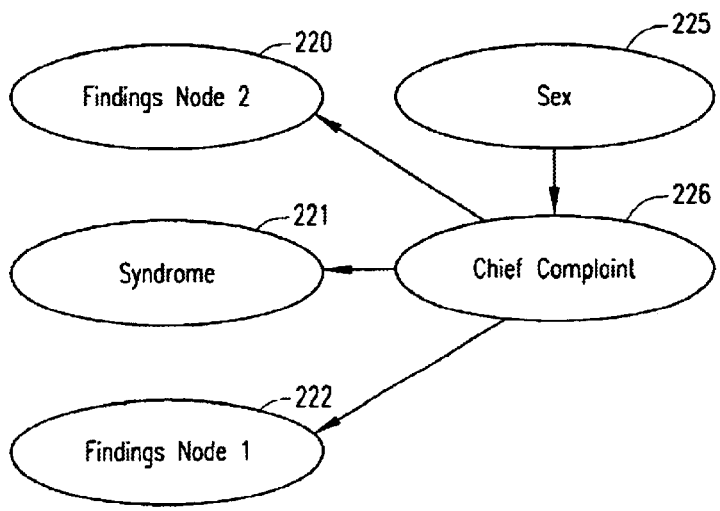
FIG. 11 is a Bayesian Network node diagram and correlated probability table showing the effects of inputting F4 in Findings Node 2 as evidence.

As can be seen in FIG. 10, if $F_4$ in Instantiable Node 1 222 is entered as evidence, $DDx_4$ is highly increased. Similarly, in FIG. 11, it can readily be seen that if F4 in Instantiable Node 2 220 is entered as evidence, $DDx_1$ is highly increased. In this example, both Instantiable Node 1 222 and Instantiable Node 2 220 express evidence on Syndrome Node 221.

Figure 12:
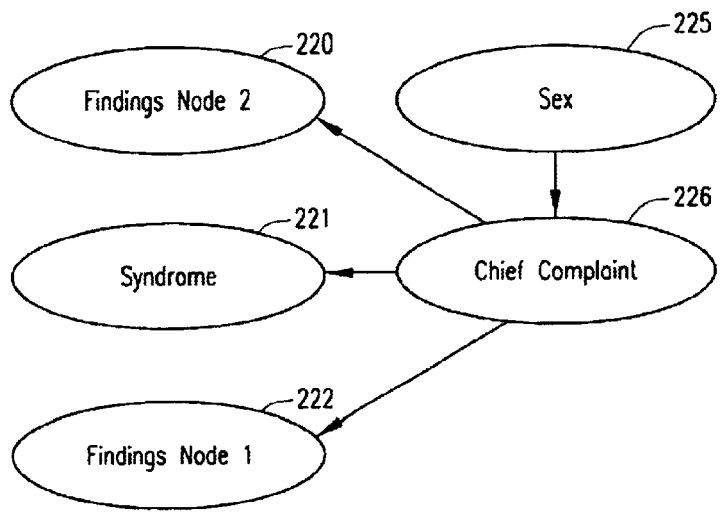
FIG. 12 is a Bayesian Network node diagram and correlated probability table showing the effects of inputting F4 in both Findings Node 1 and Findings Node 2 as evidence.

In connection with FIG. 12, if $F_4$ is entered as evidence in Instantiable Node 1 222 and Instantiable Node 2 220 at the same time, $DDx_3$ is increased to 100%, indicating that of all 16 possible combinations, $(F_4, F_4)$ is indicative of a certain syndrome which increases the probability of a disease that has a less than 1% chance of being the cause of the chief complaint if the findings were isolated events.

Intermediary Nodes and Domain Simplification

Sometimes, various input data would in fact exert pressure in the same direction, and will increase or decrease the probability of some common denominator. In such circumstances, instead of describing the effects of all pieces of evidence on the fault node separately, we could simply create a node for the common aspect of the evidence, and describe effects of that common evidence on the fault node. In this situation, an "intermediary node" may be useful.

An example of such a situation is in describing the effects of the signs and symptoms tachycardia, increased blood pressure, cold sweats, and palpitation on the domain causes for chest pain. In the Bayesian Network model, one could make direct connections between the fault node and the corresponding evidence nodes. However, it is known from physiopathology that all of these conditions are caused by catecholamine release. Therefore, one could insert an intermediary node named "catecholamine release," and connect it to the fault node. All evidence nodes will feed into this intermediary node, and will increase or decrease the chances of catecholamine release. The criteria for implementing a series of evidence nodes in this form could be expanded to encompass any series of evidence that would exert their effects on the domain in a certain foreseeable fashion, and thereby eliminate the need for a known medical association between the input evidence.

It should be further added that such intermediary nodes need not necessarily be binary (true/false), and the same is also true for evidence nodes. It should also be pointed out that by feeding in, or to, reference is not made to the direction of arrows in the directed Bayesian Network graph. It is intended to show the propagation of evidence in the Bayesian Network.

Another instance that intermediary nodes could become handy is where it is necessary to reduce the size of the table for explicit representation of domain knowledge. The reduction of table size has many self-evident advantages, some of which are the reduction in time and effort to create and maintain the table, and the reduction of instances of probabilities which are required to complete the table, but the values of which are unavailable or meaningless.

This second category of the use of intermediary nodes will be explained in an example. In a given modeling of a domain, it is necessary to exert effects of a number of risk factors on the fault node Causes for Abdominal Pain. Upon closer study of these risk factors, it becomes evident that these risk factors must be implemented explicitly. It also becomes clear that some risk factors will increase the risk for differential diagnoses associated with surgical abdomen, a condition that requires immediate surgery, and some other will increase the probabilities for differentials associated with medical abdomen, which is represented as opposing the previous one (i.e., surgery is not required, but medical attention is). Based on what has been said so far, the risk factors of each category could be grouped up accordingly. And finally, only the nodes surgical risk factor and medical risk factor will feed in the fault node. However, since this is implemented explicitly, a table will be formed in the fault node that represents explicit data for all four possible true/false combinations of the two risk factor intermediary nodes feeding in. In this table, all columns could be easily accounted for except a column that represent both risk factors being true. In an extended example if we have more that 2 nodes, the table size will grow as powers of 2, and ambiguity will exist in columns having more that one true state. To address this problem we recommend adding another intermediary node having 3 states. One state will be surgical risk factors, the other will be medical risk factor and the last one will represent the state in which no risk factor is present. An extended version of this implementation will be when we have n intermediary risk factor nodes and our new intermediary risk factor will have n+1 states. One very important side benefit of this method is that instead of having $2^n$ columns to fill in the fault node we will only have n+1 columns to fill in.

Figure 13:
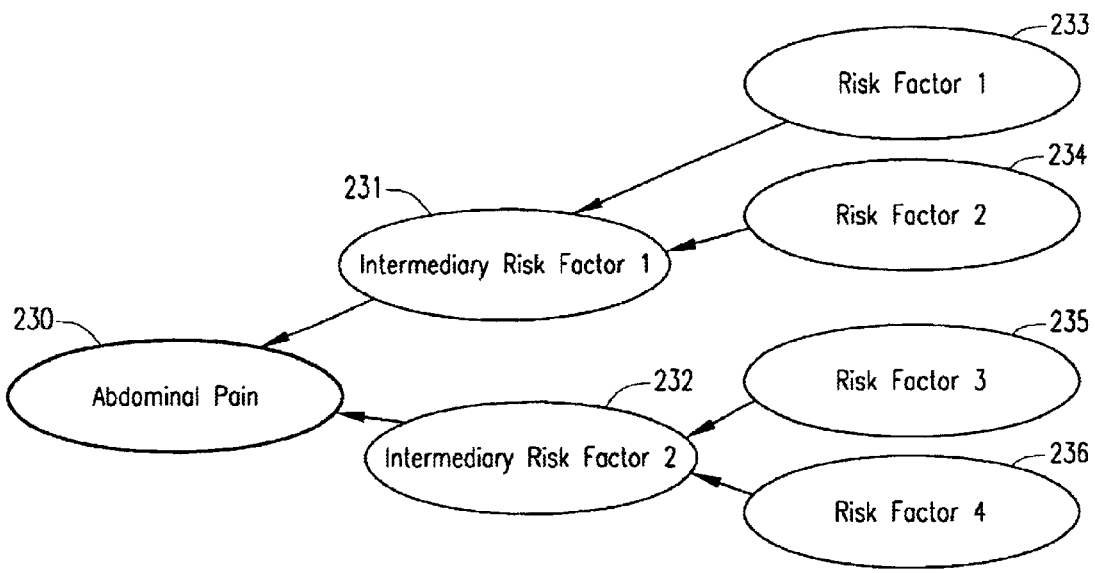
FIG. 13 is a Bayesian Network node diagram and correlated probability table showing intermediary nodes connected to the fault node separately.

As shown in FIG. 13, instantiable nodes 233, 234, 235 and 236 correspond to risk factors represented by either intermediary risk factor node 231 or 232. If intermediary risk factor nodes 231, 232 are connected to fault node 230 for abdominal pain, ambiguity will result in the situation where more that one risk factor is present. Another draw back is that the table size grows exponentially.

Figure 14:
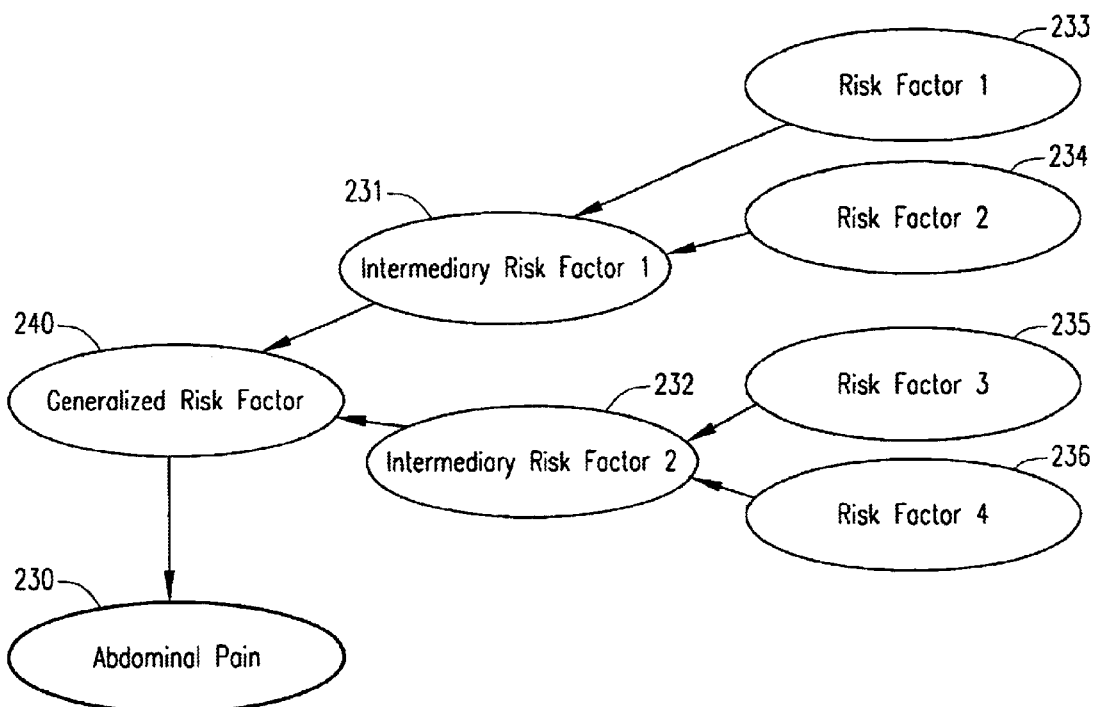
FIG. 14 is a Bayesian Network node diagram and correlated probability table showing intermediary nodes connected to the fault node via another intermediary node.

Referring now to FIG. 14, if intermediary risk factor nodes 231, 232 are connected to fault node 230 via another intermediary node 240 for generalized risk factor, the ambiguity described above is resolved. Also, this table grows linearly instead of exponentially.

Making a Decision—the Concept of Utility for Decisions

Once the questions have been asked and answered, and the fault node has provided all probabilities for different causes, the engine should provide a decision. This decision could be based on a cut-off point on probabilities of the fault node. However, the selection of a cut-off point is to an extent arbitrary and questionable. It could easily miss a critical decision by 1%. Therefore, a decision should best be made based on all the information that is available.

For this to be possible, information should be made comparable based on some arbitrary and yet acceptable means of quantification. In this vein, all different decisions may be quantified in the terms of their utility towards the purpose of the engine. For example, utility may be defined as a quantity of "expenses" or "utils" associated with any of the decisions. For purposes of description, consider four different decisions:

1. Call 911 for an ambulance;
2. Go to ER, or have someone drive you to ER;
3. Make an appointment with your doctor for next business day; and
4. Stay home and visit us later if symptoms got any worse.

Considering a diagnosis, one can define a utility value for all four of the available decisions for the diagnosis as follows:

1. If the right decision is made, a bonus is obtained. This bonus should also reflect the importance of the right decision. So if the bonus for the least important decision—in this example, decision number four—is valued at x, then utility will reflect one additional x per one level of decision criticality upward.
2. If a poor decision is made in the sense that criticality of the situation is underestimated, then a penalty is incurred. Like bonuses, the penalty should reflect the level of inappropriateness of the decision. Therefore, if the penalty for underestimating the criticality of the decision for one level is y, then utility will reflect an additional diminution y per each level of underestimation.
3. If a poor decision is made in the sense that criticality is overestimated, then again something is lost, and there is a negative utility for the decision. In this example, however, one can calculate the net loss. An example is that if the right decision is ER, and the decision is made for ambulance, then someone is unnecessary paying for an ambulance, the cost of which is readily and accurately estimated. Therefore, the negative utility here is calculated as the difference in costs of the decisions.

Theoretically, one could calculate the utility for any decision for all differential diagnosis and add them up based on their probability. In other words, one can calculate the following for all decisions:

$$U(D_j) = \sum_{i=0}^{n} P(DDx_i) \cdot U(D_j, DDx_i)$$

where $U(D_j)$ is the utility of decision $D_j$ for all differential diagnoses, $U(D_j,DDx_i)$ is the utility of decision $D_j$ for differential diagnosis $DDx_i$, and $P(DDx_i)$ is the probability of differential diagnosis $DDx_1$. The final decision (whether diagnosis, disposition, treatment or some other decision) could be made based on which decision has the greatest utility. Questioning could be stopped when all instantiable nodes are instantiated, when the remaining questions do not change our decision, or at any other statistically significant event.

Software Based on This Methodology

To facilitate use of this methodology, it is contemplated that the system and method of the present invention may be embodied in a software application. In addition to helping users follow the guidelines described above, such software might automatically generate tables based on user input relating to instantiable nodes. This input may be provided in a simple scaling format. For example, in a preferred embodiment, the domain expert can describe effects of any state of a parent node on different states of the child node in a scale of −4 to 4. In this scale, −4 means the probability of the corresponding condition is zero, and 4 means that the probability is 100%. Clearly there can be only one 4, but many −4's. At least one non −4 is necessary. Using the following formulas, the probabilities of all the cells in the probability tables could be calculated based on such scalar input.

Let $P_i$ be the probability of any cell in the table describing the probability of the state in the child node given a state in the parent node. Then the probabilities in the same column should add up to 1. Hence:

$$\sum_{i=0}^{n} P_i = 1,$$

where n=number of rows in the table

From the input date in the scaling method, one can infer that $P_i$ could be described as follows:

$P_i = p + x_i \cdot q$, with $x_i$ being the scale of a state (−4, 4)

Then:

$$\sum_{i=0}^{n} p + x_i \cdot q = n \cdot p + q \sum_{i=0}^{n} x_i = 100$$

$$\text{Let} \sum_{i=0}^{n} x_i = r$$

Then:

$n \cdot p + q \cdot r = 100$

We also know that $p - 4 \cdot q = 0$;

Hence:

$$\begin{cases} n \cdot p + q \cdot r = 100 \\ p - 4 \cdot q = 0 \end{cases}$$

If we solve this system of equations for p and q we will have:

$$p = \frac{400}{4 \cdot n + r} \text{ and } q = \frac{p}{4}$$

If in the set $x_i$, only one x is greater than −4, then $$\sum_{i=0}^{n} x_i > -4 \cdot n;$$

hence $p \geq 0$, which means that the table will not have a negative probability.

Miscellaneous Considerations

In addition to the various relations described above between the diagnosis fault node, decision nodes and instantiable nodes, a person of ordinary skill in the art would appreciate that there can be other relations between fault nodes, instantiable nodes and decision nodes. Such relationships can not be reduced to a comprehensive set, which should be considered when designing a domain model.

D-separation is another important concept that can affect the way evidence is propagated through the Bayesian Network and influence diagrams. If some nodes are d-separated from each other, it is not typically a problem unless an instantiable node is d-separated from a decision node or a fault node.

When picking questions for answers to provide to instantiable nodes, one would commonly use a simple methodology to pick the next best question or sequence of questions in actual implementation. In most circumstances, the number of questions or observables in the domain is such that they cannot be instantiated in one pass. Therefore, evidence should be input in sequences of one or more questions at a time. As a result, one must usually select the most important or critical question or questions to ask next. Usually this entails the simple procedure of selecting the most probable and most critical diagnoses as a target at any given time, and picking the next question or questions based upon the amount of impact any of the remaining questions or groups of questions will have on the probabilities of the two diagnoses, had they been instantiated.

While the invention has been described in the context of a preferred embodiment, it will be apparent to those skilled in the art that the present invention may be modified in numerous ways and may assume many embodiments other than that specifically set out and described above. Accordingly, it is intended by the appended claims to cover all modifications of the invention which fall within the true scope of the invention.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method for providing automated medical decision-making comprising:
    listing differential diagnoses for each of a plurality of conditions;
    listing the characteristics of each differential diagnosis;
    establishing a Bayesian Network modeling knowledge pertaining to said conditions, said differential diagnoses, and said characteristics, wherein the presence or absence of at least some of said conditions affects conditional probabilities that a patient under study has at least some of said diagnoses;
    generating questions to identify said presence or absence of said conditions;
    presenting said patient under study with a subset of said questions for the purpose of generating responses, wherein said subset is selected dynamically by favoring questions which have a significant statistical impact on said conditional probabilities;
    inputting said responses to said questions into said Bayesian Network; and
    calculating a diagnosis for the patient under study utilizing said Bayesian Network.

2. The method for providing automated medical decision-making of claim 1, wherein said Bayesian Network further comprises a plurality of instantiable nodes for entering evidence into said Bayesian Network.

3. The method for providing automated medical decision-making of claim 2, wherein said Bayesian Network further comprises a plurality of fault nodes to which at least some of said evidence is propagated.

4. The method for providing automated medical decision-making of claim 3, wherein said Bayesian Network further comprises a utility node.

5. The method for providing automated medical decision-making of claim 4, wherein said Bayesian Network further comprises a decision node.

6. The method for providing automated medical decision-making of claim 5, wherein said decision node generates a diagnosis for said patient under study.

7. The method for providing automated medical decision-making of claim 5, wherein said decision node generates a disposition level for said patient under study.

8. The method for providing automated medical decision-making of claim 5, wherein said decision node generates a recommended treatment for said patient under study.

9. The method for providing automated medical decision-making of claim 5, wherein said decision node generates a prognosis for said patient under study.

10. The method for providing automated medical decision-making of claim 5, wherein said Bayesian Network further comprises an intermediary node.

11. The method for providing automated medical decision-making of claim 10, wherein said intermediary node relates to a risk factor associated with a medical diagnosis.

12. The method for providing automated medical decision-making of claim 10, wherein said intermediary node is configured to reduce the number of inputs into said fault node.

13. The method for providing automated medical decision-making of claim 5, wherein said decision node generates a prognosis for said patient under study.

14. A computerized system for providing automated medical triage to a patient under study comprising:
    a server including processing means and memory means, said memory means comprising a Bayesian Network, wherein said Bayesian Network comprises a plurality of instantiable nodes, a plurality of fault nodes, a utility node and a decision node;
    a remote computer accessible by a patient under study;
    a network allowing access by said remote computer to said server;
    a scoring mechanism to adjust said probabilities in said diagnosis node responsive to information input by said patient under study into said remote computer.

15. The computerized system for providing automated medical triage of claim 14, further comprising:
    medical hardware in direct electrical communication with said remote computer, wherein said medical hardware provides additional information regarding said patient under study, said additional information being transmitted to said server via said network.

16. A method for providing automated medical decision-making comprising:
    establishing a Bayesian Network comprising:
        a plurality of instantiable nodes for entering evidence;
        a plurality of fault nodes in communication with said instantiable nodes for providing results capable of being monitored;
        a utility node for providing quantitative information to a decision node having states;
        and said decision node, wherein said decision node calculates a utility value for each of said states;
    obtaining evidence from a patient-under-study;
    entering said evidence into selected ones of said instantiable nodes;
    monitoring said fault nodes for,said results;
    using said results in said utility node; and
    outputting a result in said decision node based upon said quantitative information in said utility node.

17. The method for providing automated medical decision-making of claim 16, wherein said decision node generates a diagnosis for said patient under study.

18. The method for providing automated medical decision-making of claim 16, wherein said decision node generates a disposition level for said patient under study.

19. The method for providing automated medical decision-making of claim 16, wherein said decision node generates a recommended treatment for said patient under study.

20. The method for providing automated medical decision-making of claim 16, wherein said Bayesian Network further comprises an intermediary node.

21. The method for providing automated medical decision-making of claim 20, wherein said intermediary node relates to a risk factor associated with a medical diagnosis.

22. The method for providing automated medical decision-making of claim 20, wherein said intermediary node is configured to reduce the number of inputs into said fault node.

23. The method for providing automated medical decision-making of claim 16, wherein said step of establishing a Bayesian Network further comprises identifying a syndrome and configuring probability tables to recognize said syndrome.

* * * * *